United States Patent
Sabb et al.

(10) Patent No.: US 6,706,714 B2
(45) Date of Patent: Mar. 16, 2004

(54) 2,3,4,4A-TETRAHYDRO-1H-PYRAZINO[1,2-A] QUINOXALIN-5(6H)ONE DERIVATIVES

(76) Inventors: Annmarie Louise Sabb, 15 Meadow La., Pennington, NJ (US) 08534; Gregory Scott Welmaker, 2 Jackson Ct., Jackson, NJ (US) 08527; James Albert Nelson, 7 Decision Way West, Washington Crossing, PA (US) 18977

( * ) Notice: Subject to any disclaimer, the term of this patent is extended or adjusted under 35 U.S.C. 154(b) by 0 days.

(21) Appl. No.: 10/244,773

(22) Filed: Sep. 16, 2002

(65) Prior Publication Data

US 2003/0060468 A1 Mar. 27, 2003

Related U.S. Application Data

(60) Division of application No. 09/891,593, filed on Jun. 26, 2001, now Pat. No. 6,476,032, which is a continuation-in-part of application No. 09/455,220, filed on Dec. 6, 1999, now Pat. No. 6,372,745.

(60) Provisional application No. 60/172,234, filed on Dec. 17, 1998, now abandoned.

(51) Int. Cl.[7] .................. A61K 31/495; A61K 31/50
(52) U.S. Cl. .......................................... 514/250
(58) Field of Search ........................ 514/250

(56) References Cited

U.S. PATENT DOCUMENTS

| | | | |
|---|---|---|---|
| 4,032,639 A | 6/1977 | Freed et al. | |
| 4,089,958 A | 5/1978 | Freed et al. | |
| 4,203,987 A | 5/1980 | Freed | |
| 6,372,745 B1 | 4/2002 | Sabb et al. | |
| 2001/0051622 A1 | 12/2001 | Rosenweig-Lipson et al. | |

FOREIGN PATENT DOCUMENTS

| | | |
|---|---|---|
| EP | 0410535 | 1/1991 |
| EP | 0539209 | 4/1993 |
| WO | WO 96/23789 | 8/1996 |

OTHER PUBLICATIONS

Sleight, A.P., et al., Naunyn–Schmiedberg's Arch. Pharmacol., 343, 109–116 (1991).

Gupta, Y.K., et al., Indian J. Pharmacol., 26, 94–107 (1994).
Huff, J.R., et al., J. Med. Chem., 28(7), 945–948 (1985).
Mokrosz, J.L., et al., Pol. J. Pharmacol. Pharm., 44, 87–97 (1992).
Kumar et al., Indian Journal Chem., 17(B), 244–245 (1979).

Primary Examiner—Jerome D. Goldberg
(74) Attorney, Agent, or Firm—Kimberly R. Hild

(57) ABSTRACT

This invention provides compounds of formula I,

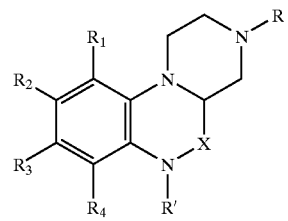

wherein

R is hydrogen or alkyl of 1–6 carbon atoms;
R' is hydrogen, alkyl of 1–6 carbon atoms, acyl of 2–7 carbon atoms, or aroyl;
$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;
X is $CR_5R_6$ or a carbonyl group;
$R_5$ and $R_6$ are each, independently, hydrogen or alkyl of 1–6 carbon atoms;
   or a pharmaceutically acceptable salt thereof, with the proviso that at least one of $R_1$, $R_2$, $R_3$, or $R_4$ are not hydrogen;
which are $5HT_{2C}$ receptor agonists useful for the treatment of disorders involving the central nervous system such as obsessive-compulsive disorder, depression, anxiety, schizophrenia, migraine, sleep disorders, eating disorders, obesity, type II diabetes, and epilepsy.

18 Claims, No Drawings

2,3,4,4A-TETRAHYDRO-1H-PYRAZINO[1,2-A]QUINOXALIN-5(6H)ONE DERIVATIVES

CROSS REFERENCE TO RELATED APPLICATIONS

This application is a divisional of U.S. application Ser. No. 09/891,593 filed on Jun. 26, 2001 now U.S. Pat. No. 6,476,032, which is a continuation-in-part of U.S. application Ser. No. 09/455,220, filed on Dec. 6, 1999 now U.S. Pat. No. 6,372,745, which claims the benefit of U.S. Provisional Application No. 60/172,234, filed Dec. 17, 1998 Abn.

BACKGROUND OF THE INVENTION

The present invention relates to derivatives of 2,3,4,4a-tetrahydro-1H-pyrazino[1,2,-a]quinoxalin-5(6H) ones which are serotonin 5-hydroxytryptamine $2_C$ ($5HT_{2C}$) receptor agonists useful for the treatment of disorders such as obsessive-compulsive disorder, depression, anxiety, schizophrenia, migraine, sleep disorders, eating disorders, obesity, type II diabetes, and epilepsy.

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the $21^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J.) 147–210 (Wiley-Liss, New York, 1991).] The $5HT_{2C}$ receptor (formerly called the $5HT_{1C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558–564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M., Williams, C., Walsh, A. E. S., Fairburn, C. G. *Nature* 376: 557 (1995).] Tecott, et al have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Dallman, M. F., Jullus, D. *Nature* 374: 542–546 (1995).] Compounds of this invention are $5HT_{2C}$ receptor subtype selective agonists which are selective over other monoamine receptors, causes a reduction in food intake and result in a reduction in weight gain. Other therapeutic indications for $5HT_{2C}$ agonists are obsessive compulsive disorder, depression, panic disorder, schizophrenia, sleep disorders, eating disorders, and epilepsy.

U.S. Pat. Nos. 4,032,639; 4,089,958; and 4,203,987 describe 2,3,4,4a-Tetrahydro-1H-pyrazino[1,2-a]quinoxalin-5(6)-ones and derivatives thereof as antihypertensive agents. In contrast, compounds of this invention bind to and activate the $5HT_{2C}$ receptors in the CNS and are useful for the treatment of CNS disorders.

Indian J. Chem. 17B, 244–245 (1979) discloses 3-Substituted 2,3,4,4a,5,6-Hexahydro-1(H)-pyrazino[1,2-a]quinoxalines which exhibit no anorexigenic or stimulant activity at 60 mg/kg i.p. dose. Weak CNS depressant activity and significant hypotensive activity in anaesthetized animals. Tachyphylaxis was observed.

DESCRIPTION OF THE INVENTION

This invention provides compounds of formula I having the structure

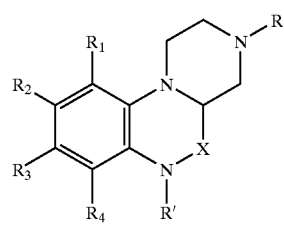

wherein wherein

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen;

which are $5HT_{2C}$ receptor agonists useful for the treatment of disorders involving the central nervous system such as obsessive-compulsive disorder, depression, anxiety, panic disorder, schizophrenia and schizophrenic disorders, migraine, sleep disorders, eating disorders, obesity, type II diabetes, and epilepsy.

This invention provides methods for treatment, inhibition or alleviation of symptoms of schizophrenic disorders in a mammal in need of such treatment. These methods include those for the schizophrenic disorders known in the art, including those defined by the American Psychiatric Associations Diagnostic and Statistical Manual of Mental Disorders, Third Edition (DSM-III, 1980), its revision DSM-III-R (1987) or the DSM-IV (1996). These methods include those for schizophrenia, schizophreniform syndromes, or schizoaffective disorders. Also included are related psychotic syndromes referred to as brief reactive psychoses, as well as borderline or latent schizophrenia and simple schizophrenia, which are also referred to as borderline or schizotypal personality disorders. Additional methods include late onset schizophrenia-like syndromes, such as the involutional paraphrenias, which are also known as paranoid disorder or atypical psychosis.

The compounds of this invention may contain an asymmetric carbon atom and some of the compounds of this invention may contain one or more asymmetric centers and may thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The term "alkyl" includes both straight- and branched-chain saturated aliphatic hydrocarbon groups. The term "aroyl" is defined as an aryl ether, where aryl is defined as an aromatic system of 6–14 carbon atoms, which may be a single ring or multiple aromatic rings fused or linked together as such that at least one part of the fused or linked rings forms the conjugated aromatic system. Preferred aryl groups include phenyl, naphthyl, biphenyl, anthryl, tetrahydronaphthyl, phenanthryl groups. Halogen is defined as Cl, Br, F, and I.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

Preferred compounds of this invention are those in which at least one of $R_1$, $R_2$, $R_3$, or $R_4$ are not hydrogen, and the non-hydrogen substituents of $R_1$, $R_2$, $R_3$, and $R_4$ are halogen or trifluoromethyl.

Preferred enantiomerically pure compounds of formulas IA and IB are provided as follows:

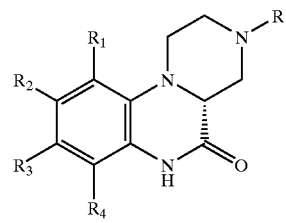

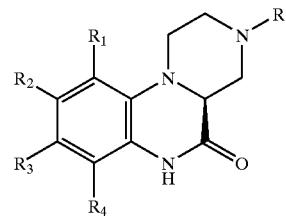

wherein R, $R_1$, $R_2$, $R_3$, and $R_4$ are as described above.

The compounds of this invention can be prepared according to the following schemes from commercially available starting materials or starting materials which can be prepared using literature procedures. These schemes show the preparation of representative compounds of this invention.

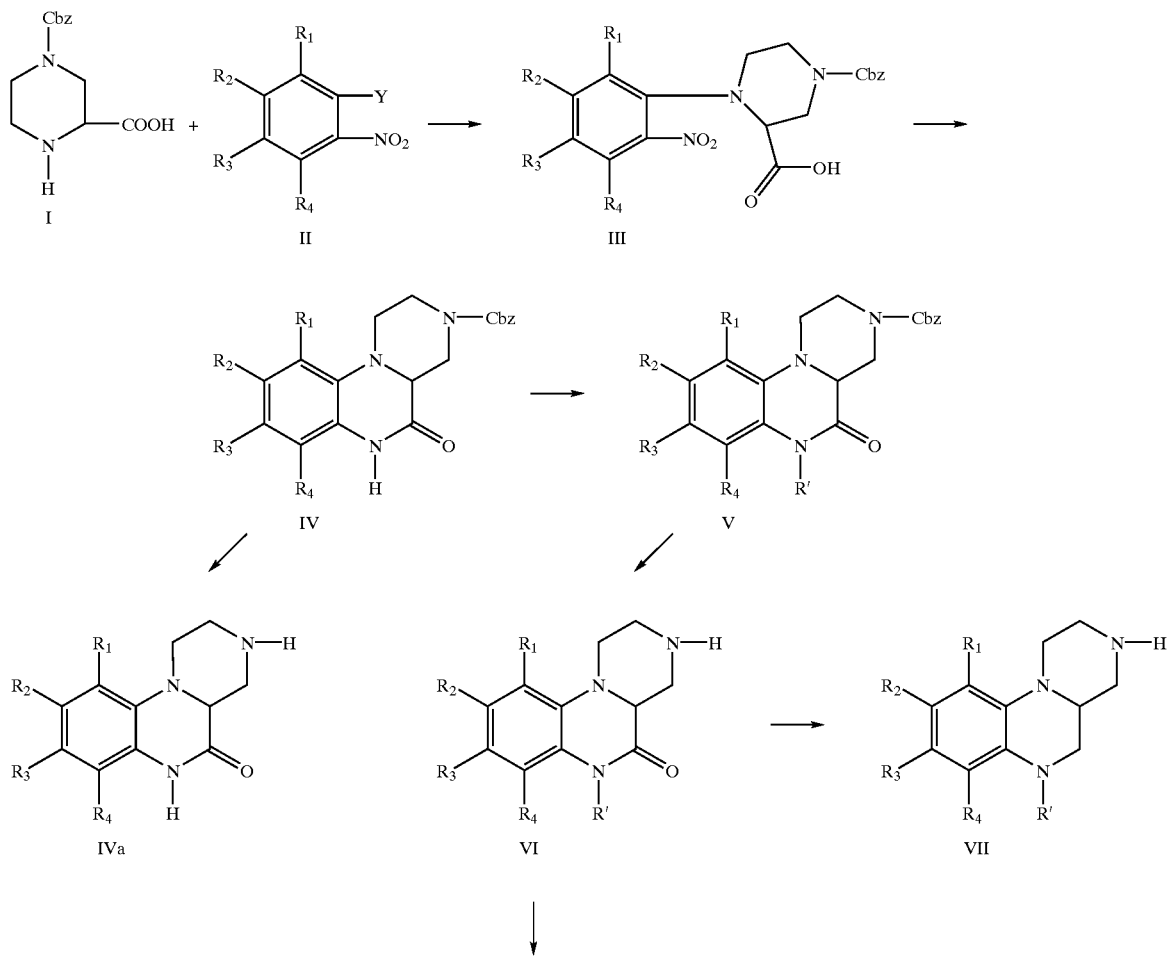

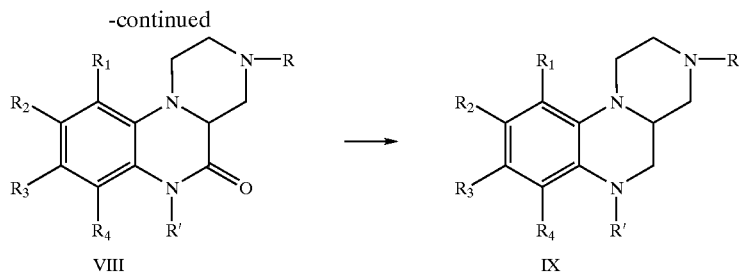

In Scheme 1, the symbol Cbz represents a carbobenzyloxy group and Y stands for chlorine, fluorine, or bromine. A solution of 4-carbobenzyloxypiperazine-2-carboxylic acid (I) is allowed to react with a substituted ortho-nitrohalobenzene (II) to give a 4-carbobenzyloxy-1-(o-nitro-substituted-phenyl)-piperazine-2-carboxylic acid (III). The reaction is carried out in an inert organic solvent, such as dimethylsulfoxide, in the presence of a base, such as triethylamine, at a temperature above ambient temperature, such as 50–150° C.

The intermediate (III) is cyclized by a process involving reduction of the nitro group to an amino group, preferably by reaction of a metal, such as iron, in an acid, such as acetic acid, followed by heating at elevated temperature, such as 50–100° C., to effect cyclization to (IV). Removal of the Cbz protecting group using boron tribromide, catalytic reduction or a base, such as potassium hydroxide, gives products of this invention (IVa). Or treatment of (IV) with a base, such as sodium hydride, followed by reaction with an alkyl halide, such as methyl iodide, give intermediates (V).

Removal of the Cbz group with boron tribromide or potassium hydroxide give compounds of this invention (VI) where R' is lower alkyl.

Compounds (VI) can also be alkylated a second time using a base, such as sodium hydride, and an alkyl halide, such as methyl iodide, to give compounds of this invention (VIII). Alternatively, compounds (VI) can be reduced with a reducing agent, such as borane in THF, to compounds of this invention (VII). Compounds (VIII) can also be reduced with borane in THF to give (IX) which are compounds of this invention.

The amide of compounds (V) can also be reduced to amines (VII) using a reducing agent, such as borane in tetrahydrofuran, at 0–50° C. Compounds (VII) are also compounds of this invention.

Likewise, the amide of compounds (VI) can be reduced to amines (VIII) which are compounds of this invention. In compounds (VI) where R' is acyl this group is put on, as already described, after reduction of amides (VI) where R' is hydrogen.

Scheme 2

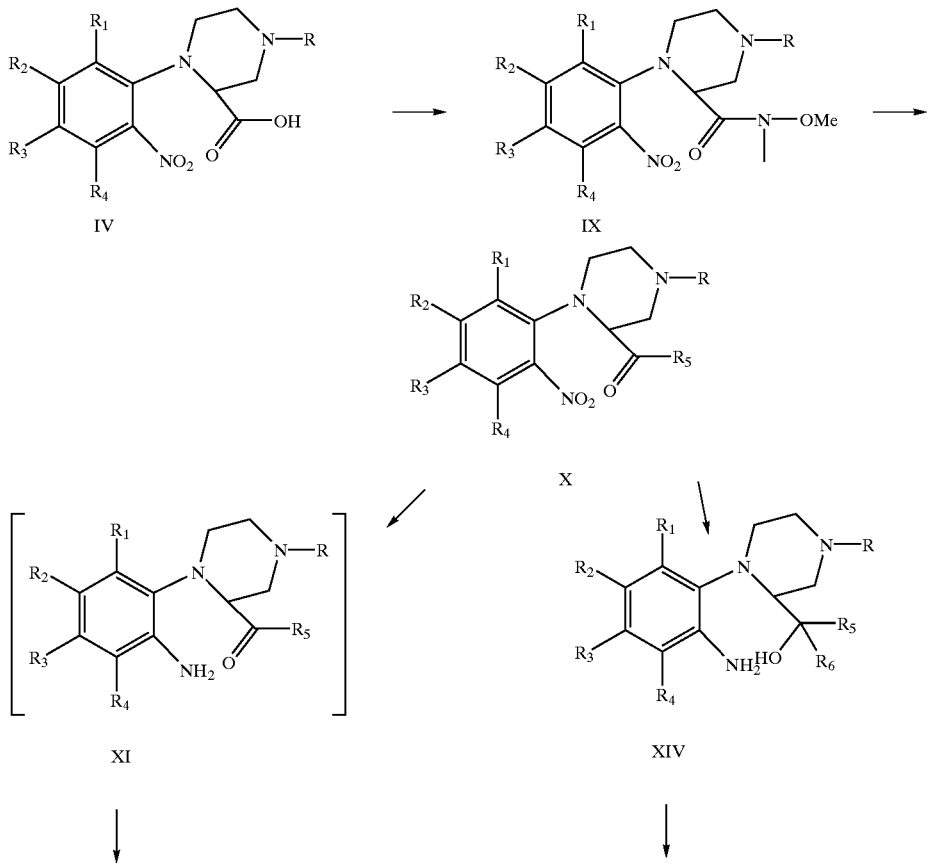

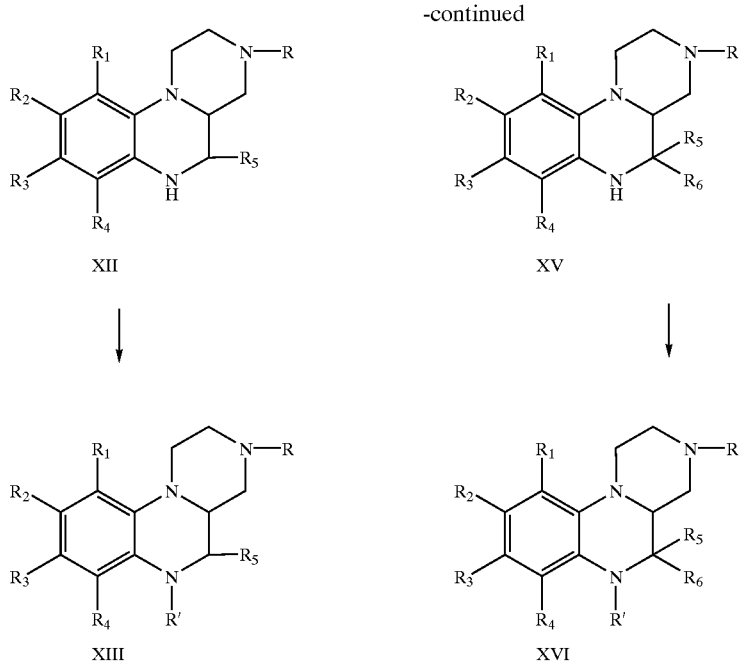

XII  XV

XIII  XVI

In Scheme 2, the carboxylic acids of intermediate (IV) are converted to the corresponding N-methoxy-N-methyl amides (IX) by reaction of the corresponding acids (IV) with N,O-dimethylhydroxylamine hydrochloride in the presence of a base, such as pyridine, and a coupling reagent, such as dicyclohexylcarbodiimide (DCC) in an organic solvent, such as methylene chloride at a temperature between 0–50° C. Treatment of intermediates (IX) with Grignard reagents or organolithium reagents, such as methyl lithium, gives ketones (X). Reduction of the nitro group in intermediates (X) with a reducing agent, such as iron in acetic acid, gives the corresponding amines (XI) which cyclize at elevated temperatures, such as 50–150° C., in the presence of an acid, such as p-toluenesulfonic acid, in an inert organic solvent, such as benzene, to give compounds of this invention (XII). Alkylation of (XII) with an alkyl halide, such as methyl iodide, or an acyl halide such as acetyl chloride, gives compounds of this invention (XIII). Treatment of intermediates (X) with a Grignard reagent, such as methylmagnesium chloride, give tertiary alcohols (XIV). Reduction of the nitro group in intermediates (XIV) with a metal, such as iron, in an acid, such as acetic acid, followed by heating at a temperature from 50–150° C., gives (XV) which are compounds of this invention. Reaction of compounds (XV) with an alkyl halide, such as methyl iodide, or an acyl halide, such as acetyl chloride, gives (XVI) which are compounds of this invention.

The enantiomerically pure compounds of this invention can be prepared according to the following Scheme 3 from commercially available starting materials or starting materials which can be prepared using literature procedures. This scheme shows the preparation of representative (R)-compounds of formula IA of this invention, starting with the known 2-(R)-piperazinecarboxylic acid (reference below). Starting from the known 2-(S)-piperazinecarboxylic acid gives the (S)-compounds of formula IB of this invention.

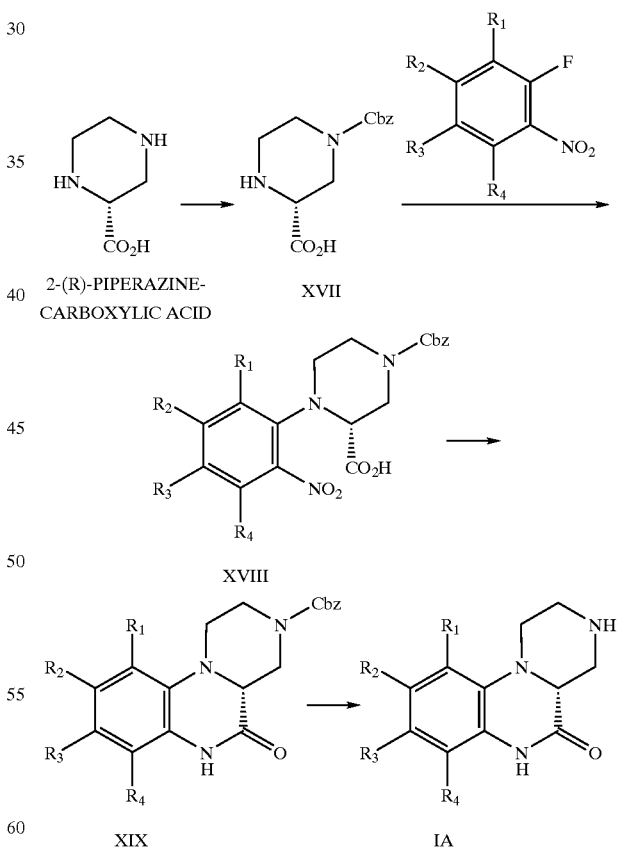

2-(R)-PIPERAZINE-CARBOXYLIC ACID

XVII

XVIII

XIX  IA

In Scheme 3, the (R)-2-piperazinecarboxylic acid (prepared according to the references below) was converted by standard methods to the N-protected amino-acid (XVII); the symbol Cbz represents a carbobenzyloxy group. A solution of (R)-4-carbobenzyloxypiperazine-2-carboxylic acid (XVII) is allowed to react with a substituted ortho-nitrofluorobenzene to give a 4-carbobenzyloxy-1-(o-nitro-substituted-phenyl)-(R)-piperazine-2-carboxylic acid (XVIII). The reaction is carried out in an inert organic solvent, such as dimethylformamide, in the presence of a base, such as triethylamine, at a temperature above ambient temperature, such as 50–70° C.

The intermediate (XVIII) is cyclized by a process involving reduction of the nitro group to an amino group, preferably by reaction of a metal, such as iron, in an acid, such as acetic acid, followed by heating at elevated temperature, such as 50–70° C., to effect cyclization to (XIX). Removal of the Cbz protecting group using 30% HBr in acetic acid, boron tribromide, or catalytic reduction, gives chiral products of this invention (IA).

The ability of the compounds of this invention to act as $5HT_{2C}$ agonists was established is several standard pharmacological test procedures; the procedures used and results obtained are provided below.

Test Procedures $5HT_{2C}$ Receptor Binding Test Procedure

To evaluate high affinity for the $5HT_{2C}$ receptor, a CHO (Chinese Hamster Ovary) cell line transfected with the cDNA expressing the human 5-hydroxy-tryptamine$_{2C}$ (h5HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 microliter ($\mu$l) volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1–2 mg per ml of suspension. The preparation membrane suspension (many times concentrated) was aliquoted in 1 ml volumes and stored at −70° C. until used in subsequent binding experiments.

Binding measurements were performed in a 96 well microtiter plate format, in a total volume of 200 $\mu$l. To each well was added: 60 $\mu$l of incubation buffer made in 50 mM Tris.HCl buffer, pH 7.4 and containing 4 mM $CaCl_2$; 20 $\mu$l of [$^{125}$I] DOI (S.A., 2200 Ci/mmol, NEN Life Science).

The dissociation constant, KD of [$^{125}$I] DOI at the human serotonin $5HT_{2C}$ receptor was 0.4 nM by saturation binding with increasing concentrations of [$^{125}$I] DOI. The reaction was initiated by the final addition of 100.0 $\mu$l of tissue suspension containing 50 $\mu$g of receptor protein. Nonspecific binding is measured in the presence of 1 $\mu$M unlabeled DOI added in 20.0 $\mu$l volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 $\mu$l Microscint-20 scintillant in a Packard TopCount® equipped with six (6) photomultiplier detectors.

Specific binding is defined as the total radioactivity bound less the amount bound in the presence of 1 $\mu$M unlabeled DOI. Binding in the presence of varying concentrations of test drugs is expressed as percent of specific binding in the absence of drug. These results are then plotted as log % bound vs log concentration of test drug. Non linear regression analysis of data points yields both the IC50 and the Ki values of test compounds with 95% confidence limits. Alternatively, a linear regression line of decline of data points is plotted, from which the IC50 value can be read off the curve and the Ki value determined by solving the following equation:

$$Ki = \frac{IC50}{1 + L/KD}$$

where L is the concentration of the radioactive ligand used and the KD is the dissociation constant of the ligand for the receptor, both expressed in nM.

The following Ki's are provided for various reference compounds:

Ki value and 95% confidence interval.

| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |
| mCPP | 6.5 (4.8–9.0) nM |
| DOI | 6.2 (4.9–8.0) nM |

Stimulation of [$^3$H] Inositol Monophosphate Production by $5HT_{2C}$ Agonists.

CHO cells transfected with the cDNA expressing the human 5-HT$_{2C}$ receptor were cultured in Dulbecco's modified Eagle's medium (DMEM) supplemented with 10% fetal bovine serum and non-essential amino acids. Upon reaching confluence the cells were harvested using PBS/EDTA and plated in 24 well plates at an initial density of 2.5×10$^5$ cells per well. One (1) ml of maintenance medium containing 1 $\mu$Ci/ml myo-[$^3$H] inositol was added to each well. After 48 hours labeling, the cells were washed once with 0.5 ml DMEM containing 25 mM HEPES and 10 mM LiCl, then preincubated with the medium for 30 min (antagonists were included in this period if tested). At the end of the preincubation, the medium was removed, the cells were then incubated with test compounds (in presence of antagonists if needed) for 30 min. The reaction was terminated by removal of the incubation solution and addition of 0.5 ml ice-cold 5% PCA, followed by 15 to 30 min incubation on ice. 200 $\mu$l of 0.5 M Tes/1.5 M $K_2CO_3$ was added to each well to neutralize to pH 7, and plates were left on ice for another 15 to 30 min to precipitate all salts. The liquid and solid phases were separated by centrifugation.

A portion (350 $\mu$l) of the upper aqueous phase was applied to Dowex AG-1X8 (formate form, 100–200 mesh) columns. The columns were then washed stepwise with 10 ml of water and 10 ml of 25 mM ammonium formate to remove free myo-[$^3$H]inositol and deacylated phosphoinositol, respectively. Finally 10 ml of 0.2 M ammonium formate solution was applied to the columns to elute [$^3$H] inositol monophosphate ([$^3$H] IP$_1$) directly into scintillation vials. Of this eluate, 1 ml was used to determine radioactivity by scintillation counting.

Agonist-stimulated levels of [$^3$H]inositol monophosphate (IP$_1$) is expressed as a percentage of the response observed with a maximally effective concentration of 5-HT (10 $\mu$M). A 3-parameter logistic function is used to generate estimate of EC$_{50}$/IC$_{50}$. Antagonists are tested in the presence of 10 $\mu$M 5-HT.

The following data are provided for various reference compounds:

| 5-HT | 15.1 nM | EC$_{50}$ |
|---|---|---|
| mCPP | 46.8 nM | EC$_{50}$ |
|  | 60% | E$_{MAX}$ (relative to 5-HT) |
| SB200646 | 286 nM | IC$_{50}$ (10 $\mu$M 5-HT as agonist) |

Effects of Compounds on Feeding Behavior in Rats

Eight (8) male Sprague-Dawley rats weighing 150–180 g were separated into individual cages and acclimated to a powdered diet for 2 weeks. During this period and throughout the test procedure, the food cup and the animals were weighed daily. Following the acclimation period, animals were fasted for 24 hours and then injected with either vehicle or one of 4 doses of the test compound. Food intake was assessed at 2 and 24 hours following compound administration. Compounds to be evaluated were injected 1–2×per week until all animals had received all doses of the test compound. The order of doses were chosen using to a modified Latin Square design. Additional studies may be conducted in satiated rats at the start of the dark cycle. Compounds were injected i.p, s.c. or p.o. At the end of the study effects of the test compound on food intake was evaluated using a repeated measures ANOVA. Data were collected were 2 hour food intake (g). Data were subjected to one-way ANOVA with posthoc t-tests to assess group differences. Where appropriate, ED50 values were calculated. The ED50 value is the dose that produces a 50% reduction in food intake during the test period.

Results

Results from In Vitro Test Procedures

| Compound | 5HT$_{2C}$ Affinity DOI/Agonist binding (Ki, nM) | 5HT$_{2C}$ % Emax (5HT, 100%) | Stimulation of IP3 (EC50, nM) |
|---|---|---|---|
| Example 1 | 4.33 | 107.50 | 12.00 |
| Example 2 | 4.18 | 112.50 | 7.92 |
| Example 3 | 66.40 | 89.00 | 289.50 |
| Example 4 | 1.00 | 99.00 | 7.32 |
| Example 5 | 7.00 | 100.00 | 33.80 |
| Example 6 | 8.00 | 77.00 | 23.20 |
| Example 7 | 8.00 | 100.00 | 97.30 |
| Example 8 | 516.00 | 85.00 | 2607.00 |
| Example 9 | 25.00 | 100.00 | 18.80 |
| Example 10 | 1036.00 | ND* | ND |
| Example 11 | 19.79 | 73% @ 1 $\mu$M | ND |
| Example 12 | 9.00 | 95.00 | 30.00 |
| Example 13 | 91.00 | ND | ND |

*ND = Not determined.

Results from In Vivo 5HT$_{2C}$ Food Intake in Rats (24 hr Fast)

| Compound | Route of Admin. | ED50 (mg/kg) |
|---|---|---|
| Example 1 | ip | 1.91 |
|  | po | 9.73 |
| Example 2 | ip | 1.99 |
| Example 11 | ip | 9.99 |

The results obtained in this standard pharmacological test procedures demonstrate that the compounds of this invention are 5HT$_{2C}$ receptor agonists useful for the treatment of diseases involving the central nervous system such as obsessive-compulsive disorder; depression; anxiety; panic disorder; schizophrenia; migraine; sleep disorders, such as sleep apnea; eating disorders, such as hyperphagia; obesity; type II diabetes; and epilepsy.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lecithins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 μg/kg-750 μg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of a representative compound of this invention.

EXAMPLE 1

8,9-Dichloro-2,3,4,4a-Tetrahydro-1H-Pyrazino[1,2-a]Quinoxalin-5(6H)-One

A. 4-Carbobenzyloxypiperazine-2-Carboxylic Acid, Copper Chelate

To a solution of 10 g of piperazine-2-carboxylic acid in 40 mL of $H_2O$ is added 39 mL of 2.5 N NaOH. A solution of 6.5 g of $CuSO_4.5H_2O$ in 80 mL of $H_2O$ is then introduced and the resulting deep blue solution is cooled to 0° C. To this cooled solution is added 5 g of solid $NaHCO_3$ in one portion followed by the dropwise addition of a solution of 7.7 mL of benzylchloroformate in 40 mL of dioxane over 10 minutes. The pH is monitored and $NaHCO_3$ is added as needed to maintain a basic solution. The ice bath is then removed and the reaction mixture is stirred overnight at ambient temperature. The blue precipitate is filtered and the solid is washed with cold $H_2O$ (20 mL), EtOH (20 mL), and EtOAc (20 mL) to give 10.4 g of a light blue solid.

B. 4-Carbobenzyloxy-1-(4,5-Dichloro-2-Nitrophenyl) Piperazine-2-Carboxylic Acid

A mixture of 10.4 g of 4-carbobenzyloxypiperazine-2-carboxylic acid, copper chelate and 7.9 g of ethylenediaminetetraacetic acid, disodium salt in 800 mL of $H_2O$ is heated to 80° C. for 3 hours. After cooling to room temperature, the mixture is concentrated to dryness. A mixture of this solid, 7.3 g of 1,2-dichloro-4-fluoro-5-nitrobenzene, and 20 mL of triethylamine in 100 mL of dimethylsulfoxide is heated to 60° C. for 12 hours. After cooling to ambient temperature, the resulting mixture is treated with HCl to pH 3. The mixture is then diluted with $H_2O$ and extracted with ethyl acetate. The combined extracts are dried over $MgSO_4$ and concentrated to give 16 g of crude product.

C. 3-Carbobenzyloxy-8,9-Dichloro-2,3,4,4a-Tetrahydro-1H-Pyrazino[1,2-a]Quinoxalin-5(6H)-One A rapidly stirred solution of 16 g of 4-carbobenzyloxy-1-(4,5-dichloro-2-nitrophenyl)piperazine-2-carboxylic acid in 200 mL of acetic acid is heated to 60° C. and then 16 g of iron powder is added in portions. The reaction mixture is stirred at 60° C. for 3 hours and then allowed to cool to room temperature. The mixture is diluted with 1 N HCl and the resulting precipitate is collected. The solid is washed with water and ether to give 11 g of product. The crude $^1H$ NMR is consistent. A small amount (1 g) of the product is purified by flash column chromatography (gradient elution with 25% ethyl acetate-hexanes to 100% ethyl acetate) to give an analytically pure sample.

$^1H$ NMR (400 MHz, $d_6$-DMSO) δ 10.8 (s, 1H); 7.39–7.31 (m, 5H); 7.04 (s, 1H); 6.96 (s, 1H); 5.12 (s, 2H); 4.38 (d, 1H, J=13.0 Hz); 4.06 (d, 1H, J=13.1 Hz); 3.71 (d, 1H, J=11.5 Hz); 3.63 (dd, 1H, J=11.2, 3.7 Hz); 2.99 (brs, 2H); 2.68 (dt, 1H, J=12.1, 3.6 Hz).

IR (KBr) 3400, 3250, 2800, 1690, 1500, 1370, 1240, 1130, 860, 770, 730 cm$^{-1}$.

MS (ESI, m/e (%)) 406 (100, [M+H]$^+$), 408 (65, [M+H]$^+$).

Anal. Calc'd for $C_{19}H_{17}Cl_2N_3O_3$: C, 56.17; H, 4.22; N, 10.34. Found: C, 55.95; H, 3.88; N, 10.29.

D. 8,9-Dichloro-2,3,4,4a-Tetrahydro-1H-Pyrazino[1,2-a]Quinoxalin-5(6H)-One

A solution of 20 g of KOH in 50 mL of $H_2O$ is added to a solution of 4.2 g of 3-carbobenzyloxy-8,9-dichloro-2,3,4,4a-tetrahydro-1H-pyrazino[1,2-a]quinoxalin-5(6H)-one in 50 mL of methanol. The resulting reaction mixture is heated to reflux for 3 hours and then is allowed to cool to ambient temperature. The solution is concentrated and the crude solid is partitioned between water and ethyl acetate. The phases are separated and the aqueous phase is extracted with ethyl acetate. The combined organic phases are concentrated. The crude solid is dissolved in a minimum amount of hot ethanol and then a solution of HCl in ethanol is added to pH 3. The solid is collected and dried in a vacuum oven at 80° C. to give 2.4 g of product as its hydrochloride salt.

$^1H$ NMR (400 MHz, $d_6$-DMSO) δ 11.0 (s, 1H); 9.51 (br s, 2H); 7.12 (s, 1H); 7.02 (s, 1H); 4.02 (dd, 1H, J=11.5, 3.4 Hz); 3.88 (d, 1H, J=11.0 Hz); 3.61 (m, 1 H); 3.41 (d, 1H, J=9.8 Hz); 3.15–2.98 (m, 3H).

IR (KBr) 3420, 3200, 3020, 2970, 2800, 1695, 1500, 1460, 1430, 1395, 1375, 1290, 1140 cm$^{-1}$.

MS (APCI, m/e (%)) 272 (100, [M+H]$^+$), 274 (65, [M+H]$^+$).

Anal. Calc'd for $C_{11}H_{12}Cl_3N_3O$: C, 42.81; H, 3.92; N, 13.62. Found: C, 42.66; H, 3.75; N, 13.33

EXAMPLE 2

(R)-8,9-Dichloro-2,3,4,4a-Tetrahydro-1H-Pyrazino[1,2-a]Quinoxalin-5(6H)-One

Method A (Separation Method)

The enantiomers of the compound of Example 1 were separated by HPLC using a Chiracel AD column with 100% ethanol at a flow rate of 0.5 mL/min to provide the compounds of Example 2 and 3. The first enantiomer (Example 2) elutes at 10.4 min ($[\alpha]^{25}_D$+27.8) and the second (Example 3) at 13.7 min ($[\alpha]^{25}_D$−25.5).

Method B (Chiral Synthesis)

A. (R)-4-Carbobenzyloxypiperazine-2-Carboxylic Acid.

To a solution of 5.0 g of (R)-piperazine-2-carboxylic acid[1] in 30 mL of water is added 5.0 g $CuSO_4.5H_2O$ dissolved in 60 mL of $H_2O$. The solution is cooled to 0–5° C. and 10.0 g of $NaHCO_3$ is added followed by the addition of 5.3 g of benzylchloro-formate in 40 mL of acetone over 90 minutes. The mixture is warmed to ambient temperature and stirred for 24 h. The blue precipitate is filtered and the solid is washed with cold water. The solids are slurried in 100 mL of 1:1 methanol: water mixture and the pH adjusted to <4 by the addition of 2.5 N HCl. The solution is applied to a column of 400 g of AG 50W-8X resin that had been pre-washed with a mixture of 1:16:16 pyridine: methanol: water. The product was eluted with the same solvent mixture and the combined product fractions are concentrated under reduced pressure (<50° C.) to give a semi-solid residue. This material is slurried with 50 mL of ethanol to obtain crystalline solid. The solids are collected and dried to give 6.0 g (59.5%) of white solid, mp 246–8° C. decomposed.

[1] E. Felder, S. Maffei, S. Pietra, D. Pitre, *Helv. Chim. Acta.* 1960, 888–896.

$H^1$ NMR (400 Hz, $d_6$-DMSO) δ 7.37–7.30 (m, 5H); 5.08 (s, 2H); 4.19 (d, 1H, J=12.1 Hz); 3.89 (d, 1H, J=13.8); 3.27 (dd, 1H, J=11.0, 4.0 Hz); 3.08 (m, 3H); 2.82 (dt, 1H, J=12.2, 3.6 Hz).

IR (KBr) 3050, 1700, 1620, 1430, 1400, 1235, 1150 cm$^{-1}$.

MS (ESI(+), m/e (%)) 265 (100, [M+H]$^+$).

Anal. Calc'd for $C_{13}H_{16}N_2O_4$: C, 59.08; H, 6.10; N, 10.60. Found: C, 59.04; H, 6.09; N, 10.40.

Chiral Purity=99.99% (HPLC: Chiralcel WH, 4.6×25 mm).

$[\alpha]_D$=−38.77° (c=1, $H_2O$).

B. (R)-4-Carbobenzyloxy-1-(4,5-Dichloro-2-Nitrophenyl)-Piperazine-2-Carboxylic Acid.

To a slurry containing 5.0 g of (R)-4-carbobenzyloxypiperazine-2-carboxylic acid, 4.2 g of 1,2-dichloro-fluoro-5-nitrobenzene, 85 mL of water and 170 mL of dimethylformamide is added slowly 5.3 mL of triethylamine. The solution is heated to 50° C. for 5 hours, then at ambient temperature overnight. The dark orange solution is concentrated under reduced pressure (1–2 mm, <50° C.) to an orange oily residue. This oil is dissolved in 400 mL of ethyl acetate and washed with 100 mL of 1 N HCl (2×), with 150 mL of water (2×), and 100 mL of brine. The organic layer is dried over $MgSO_4$, filtered and concentrated to give 8.1 g (94.2%) of title compound as an orange solid foam.

MS (ESI(+), m/e (%)) 454 (40, [M+H]$^+$), 456 (35, [M+H]$^+$), 471 (100, [M+$NH_4$]$^+$) and 473 (100, [M+$NH_4$]$^+$).

Chiral Purity=99.99% (HPLC: Whelk-O, 4.6×250 mm).

C. (R)-Carbobenzyloxy-8,9-Dichloro-2,3,4,4a-Tetrahydro-1H-Pyrazino[1,2a]Quinoxalin-5(6H)-One.

To a solution of 8.0 g (R)-4-carbobenzyloxy-1-(4,5-dichloro-2-nitrophenyl)-piperazine-2-carboxylic acid in 200 mL of acetic acid is added 6.0 g of iron powder. With good stirring, the mixture is heated at 60° C. for 2 hours, followed by concentrated under reduced pressure (1–2 mm, <40° C.) to a gray-black residue. This material was slurried with 400 mL of ethyl acetate and filtered. This process was repeated. The combined ethyl acetate filtrates are washed with 150 mL of 1 N HCl, 200 mL of water (2×), 200 mL of brine and dried over $MgSO_4$. Filtration and concentration of the solvent gave a semi-solid material that is crystallized from ethyl acetate-hexane to afford 5.44 g (76.1%) of title compound as a white solid, mp 136–138° C.

$H^1$ NMR (400 Hz, $d_6$-DMSO) δ 10.81 (s, 1H); 7.38–7.31 (m, 5H); 7.04 (s, 1H); 6.95 (s, 1H); 5.11 (s, 2H); 4.37 (d, 1H, J=12.5 Hz); 4.05 (d, 1H, J=13.4 Hz); 3.70 (d, 1H, J=11.2 Hz); 3.63 (dd, 1H, J=3.6, 10.8 Hz); 3.00 (bs, 2H); 2.66 (dt, 1H, J=3.6, 12.2 Hz).

IR (KBr) 3240, 1710, 1675, 1500, 1300, 1245, 1130 cm$^{-1}$.

MS (APCI, m/e (%)) 406 (100, [M+H]$^+$) and 408 (90, [M+H]$^+$).

Anal. Calc'd for $C_{19}H_{17}Cl_2N_3O_3$: C, 56.17; H, 4.27; N, 10.34. Found: C, 55.97; H, 4.33; N, 9.90.

Chiral Purity=99.99% (HPLC: Chiralcel AD, 4.6×250 mm).

$[\alpha]_D$=+23.89° (c=1, $CHCl_3$).

D. (R)-8,9-Dichloro-2,3,4,4a-Tetrahydro-1H-Pyrazino[1,2a]Quinoxalin-5(6H)-One.

To a solution of 5.0 g of (R)-carbobenzyloxy-8,9-dichloro-2,3,4,4a-tetrahydro-1H-pyrazino-[1,2a]quinoxalin-5(6H)-one in 100 mL of acetic acid is added dropwise 15 mL of 30% HBr in acetic acid. The solution is stirred at ambient temperature for 5 hour and concentrated under reduced pressure (1 mm, <40° C.) to give solid residue. The residue is dissolved in 300 mL of ethyl acetate and washed with 100 mL of 1 N NaOH, 200 mL of water (2×) and 300 mL of brine and dried over $MgSO_4$. Filtration and concentration of the solvent affords 3.59 g (99%) of crude free base. Purification by column chromatography (265 g of silica gel, 9:1 ethylacetate: 2M $NH_3$ in methanol) gives 1.8 g (54.9%) of product as a yellowish solid, mp 203° C. decomposed. The solid (1.6 g) was dissolved in 50 mL of methanol and treated with an excess of 1 M HCl in ether to afford 1.6 g (88.2%) of the hydrochloride salt as an off-white solid, mp >290° C.

$H^1$ NMR (400 Hz, $d_6$-DMSO) δ 11.00 (s, 1H); 9.58 (s, 2H); 7.12 (s, 1H); 7.02 (s, 1H); 4.03 (dd, 1H, J=11.6, 3.6 Hz); 3.87 (d, 1H, J=10.7 Hz); 3.61 (dd, 1H, J=12.9, 2.0 Hz); 3.41 (d, 1H, J=9.5 Hz); 3.42–2.99 (m, 3H).

IR (KBr) 2950, 2700, 1700, 1590, 1500 cm$^{-1}$.

MS (APCI, m/e (%)) 272 (100, [M+H]$^+$) and 274 (65, [M+H]$^+$).

Anal. Calc'd for $C_{11}H_{11}Cl_2N_3O.HCl$: C, 42.81; H, 3.92; N, 13.62. Found: C, 42.45; H, 3.78; N, 13.43.

Chiral Purity=99.99% (HPLC: Chiralcel AD, 4.6×250 mm).

$[\alpha]_D$=+27.72° (c=1, DMSO).

EXAMPLE 3

(S)-8,9-Dichloro-2,3,4,4a-Tetrahydro-1H-Pyrazino[1,2-a]Quinoxalin-5(6H)-One

Method A (Separation Method)

The enantiomers of the compound of Example 1 were separated by HPLC using a Chiracel AD column with 100% ethanol at a flow rate of 0.5 mL/min to provide the compounds of Example 2 and 3. The first enantiomer (Example 2) elutes at 10.4 min ($[\alpha]^{25}_D$+27.8) and the second (Example 3) at 13.7 min ($[\alpha]^{25}_D$−25.5).

Method B (Chiral Synthesis)

A. (S)-4-Carbobenzyloxypiperazine-2-Carboxylic Acid.

To a solution of 4.0 g of (S)-piperazine-2-carboxylic acid[1] in 70 mL of water is added 4.2 g of $CuCl_2$. The pH of the blue solution is adjusted to 10 by the addition of 2.5 N NaOH and 70 mL of acetone is added. The solution is cooled to 0–5° C. and 5.3 g of benzylchloroformate in 40 mL of acetone is added over 90 minutes. The pH is monitored and maintained by the addition of 1 N NaOH. The mixture is warmed to ambient temperature and stirred overnight. The blue precipitate is filtered and the solid is washed with cold water. The solids are slurried in 100 mL of 1:1 methanol: water mixture and the pH adjusted to <4 by the addition of 2.5 N HCl. The solution is applied to a column of 400 g of AG 50W-8X resin that had been pre-washed with a mixture of 1:16:16 pyridine: methanol: water. The product was eluted with the same solvent mixture and the combined product fractions are concentrated under reduced pressure (<50° C.) to give a semi-solid residue. This material is slurried with 50 mL of methanol to obtain crystalline solids. The solids are collected and dried to give 4.0 g (50%) of white solid, mp 247° C. decomposed.

[1] E. Felder, S. Maffei, S. Pietra, D. Pitre, *Helv. Chim. Acta.* 1960, 888–896.

$H^1$ NMR (400 Hz, $d_6$-DMSO) δ 7.37–7.30 (m, 5H); 5.08 (s, 1H); 4.19 (d, 1H, J=12.1 Hz); 3.89 (d, 1H, J=13.8); 3.27 (dd, 1H, J=11.0, 4.0 Hz); 3.08 (m, 3H); 2.82 (dt, 1H, J=12.2, 3.6 Hz).

IR (KBr) 3200, 1700, 1620, 1430, 1400, 1235, 1150 cm$^{-1}$.

MS (APCI, m/e (%)) 263 (100, [M–H]$^-$).

Anal. Calc'd for $C_{13}H_{16}N_2O_4$: C, 59.08; H, 6.10; N, 10.60. Found: C, 58.90; H, 6.20; N, 10.58.

Chiral Purity=99.88% (HPLC: Chiralcel WH, 4.6×25 mm).

B. (S)-4-Carbobenzyloxy-1-(4,5-Dichloro-2-Nitrophenyl)-Piperazine-2-Carboxylic Acid.

To a slurry containing 1.5 g of (S)-4-carbobenzyloxypiperazine-2-carboxylic acid, 1.25 g of 1,2-dichloro-fluoro-5-nitrobenzene, 25 mL of water and 50 mL of dimethylformamide is added slowly 1.6 mL of triethylamine. The solution is heated to 50° C. for 5 hours, then at ambient temperature over night. The dark orange solution is concentrated under reduced pressure (1–2 mm, <50° C.) to an orange oily residue. This oil is dissolved in 100 mL of ethyl acetate and washed with 20 mL of 1 N HCl (2×), with 100 mL of water (2×), and 100 mL of brine. The organic layer is dried over MgSO$_4$, filtered and concentrated to give 2.5 g (99%) an orange solid foam.

MS (APCI, m/e (%)) 452 (100, [M–H]$^-$) and 454 (75, [M–H]$^-$).

Anal. Calc'd for $C_{19}H_{17}Cl_2N_3O_6$·0.5 H$_2$O: C, 49.26; H, 3.92; N, 9.07. Found: C, 48.90; H, 3.80; N, 8.74.

Chiral Purity=99.99% (HPLC: Whelk-O, 4.6×250 mm).

$[α]_D$=–64.2° (c=1, MeOH).

C. (S)-Carbobenzyloxy-8,9-Dichloro-2,3,4,4a-Tetrahydro-1H-Pyrazino[1,2a]Quinoxalin-5(6H)-One.

To a solution of 1.5 g (S)-4-carbobenzyloxy-1-(4,5-dichloro-2-nitrophenyl)-piperazine-2-carboxylic acid in 40 mL of acetic acid is added 1.2 g of iron powder. With good stirring, the mixture is heated at 60° C. for 2 hours, then concentrated under reduced pressure (1–2 mm, <40° C.) to a gray-black residue. This material was slurried with 100 mL of ethyl acetate (2×). The combined ethyl acetate filtrates are washed with 100 mL of 1N HCl, 200 mL of water (2×), 100 mL of brine and dried over MgSO$_4$. Filtration and concentration of the solvent gave a semi-solid material that is crystallized from hexane to afford 1.08 g (80.6%) of title compound as a white solid, mp 174–6° C.

$H^1$ NMR (400 Hz, $d_6$-DMSO) δ 10.93 (s, 1H); 7.41–7.31 (m, 5H); 7.04 (s, 1H); 6.95 (s, 1H); 5.11 (s, 1H); 4.37 (d, 1H, J=12.5 Hz); 4.05 (d, 1H, J=13.4 Hz); 3.70 (d, 1H, J=11.2 Hz); 3.63 (dd, 1H, J=3.6, 10.8 Hz); 3.00 (bs, 2H); 2.66 (dt, 1H, J=3.6, 12.2 Hz).

IR (KBr) 3240, 1710, 1675, 1500, 1300, 1245, 1130 cm$^{-1}$.

MS (APCI, m/e (%)) 406 (70, [M+H]$^+$) and 408 (45, [M+H]$^+$).

Anal. Calc'd for $C_{19}H_{17}Cl_2N_3O_3$: C, 56.17; H, 4.27; N, 10.34. Found: C, 56.26; H, 4.18; N, 10.37.

Chiral Purity=99.9% (HPLC: Chiralcel AD, 4.6×250 mm).

D. (S)-8,9-Dichloro-2,3,4,4a-Tetrahydro-1H-Pyrazino[1,2a]Quinoxalin-5(6H)-One.

To a solution of 0.155 g of (S)-carbobenzyloxy-8,9-dichloro-2,3,4,4a-tetrahydro-1H-pyrazino-[1,2a]quinoxalin-5(6H)-one in 8 mL of acetic acid is added dropwise 1.5 mL of 30% HBr in acetic acid. The solution is stirred at ambient temperature for 2.5 hour and concentrated under reduced pressure (1 mm, <40° C.) to afford 0.18 g of tan solid. The solids dissolved in 50 mL of ethyl acetate and washed with 10 mL of 1 N NaOH, 20 mL of water (2×) and 30 mL of brine and dried over MgSO$_4$. Filtration and concentration of the solvent affords 0.056 g (53.8%) of title compound as a white solid.

$H^1$ NMR (400 Hz, $d_6$-DMSO) δ 10.63 (s, 1H); 6.96 (s, 1H); 6.92 (s, 1H); 3.49 (bd, 1H, J=10.0 Hz); 3.41 (dd, 1H, J=10.5, 3.5 Hz); 3.29 (m, 1H); 2.94 (bd, 1H, J=9.9 Hz) 2.67–2.53 (m, 4H).

MS (APCI, m/e (%)) 272 (100, [M+H]$^+$) and 274 (55, [M+H]$^+$).

Chiral Purity=99.9% (HPLC: Chiralcel AD, 4.6×250 mm).

$[α]_D$=–25.5° (c=1, DMSO).

EXAMPLE 4

8,9-Dichloro-2,3,4,4a,5,6-Hexahydro-1H-Pyrazino[1,2-a]Quinoxaline, Dihydrochloride A solution of 5 mL of 1 M BH$_3$·THF in THF was added to a cooled (0° C.) solution of 0.43 g of 8,9-dichloro-2,3,4,4a-tetrahydro-1H-pyrazino[1,2-a]quinoxalin-5(6H)-one in 20 mL of THF. The resulting solution was allowed to gradually warm to room temperature overnight. The reaction was quenched with methanol and concentrated. The crude material was dissolved in methanol and again concentrated. The product was purified by flash column chromatography through silica gel (elution with 40% ethyl acetate-hexanes) to afford 0.30 g (73%). The material was dissolved in ethanol and HCl in EtOH was added until the solution was acidic. Diethyl ether was then added until a precipitate formed. The solid was collected and dried under vacuum to give 68 mg of product as the dihydrochloride salt.

[1] H NMR (400 MHz, $d_6$-DMSO) δ 9.44–9.35 (m, 2H); 6.86 (s, 1H); 6.59 (s, 1H); 3.78 (d, 1H, J=11.8 Hz); 3.37–3.24 (m, 4H); 3.07–2.89 (m, 3H); 2.69 (m, 1H).

IR (KBr) 3380, 3190, 2970, 2810, 2750, 2400, 1600, 1500, 1450, 1380, 1270, 1140, 1110 cm$^{-1}$.

MS (APCI, m/e (%)) 258 (100, [M+H]$^+$), 260 (65, [M+H]$^+$).

EXAMPLE 5

(R)-8,9-Dichloro-2,3,4,4a,5,6-Hexahydro-1H-Pyrazino[2-a]Quinoxaline, Dihydrochloride By the same procedure described for Example 4, 1.8 g of (R)-8,9-dichloro-2,3,4,4a-tetrahydro-1H-pyrazino[1,2-a]quinoxalin-5(6H)-one was reduced to give 0.77 g of product.

The enantiomers were be separated by HPLC using a Chirapak AD column with 100% methanol at a flow rate of 0.8 mL/min. The first enantiomer eluted at 7.2 min and the second at 8.9 min.

HPLC analysis indicated an ee of >99% (7.2 min retention time).

$^1$H NMR (400 MHz, $d_6$-DMSO) δ 9.44–9.35 (m, 2H); 6.86 (s, 1H); 6.59 (s, 1H); 3.78 (d, 1H, J=11.8 Hz); 3.37–3.24 (m, 4 H); 3.07–2.89 (m, 3H); 2.69 (m, 1 H).

IR (KBr) 3380, 3190, 2970, 2810, 2750, 2400, 1600, 1500, 1450, 1380, 1270, 1140, 1110 cm$^{-1}$.

MS (APCI, m/e (%)) 258 (100, [M+H]$^+$), 260 (65, [M+H]$^+$).

EXAMPLE 6
(S)-8,9-Dichloro-2,3,4,4a,5,6-Hexahydro-1H-Pyrazino[1,2-a]Quinoxaline, Dihydrochloride By the same procedure described for Example 4, 0.80 g of (S)-8,9-dichloro-2,3,4,4a-tetrahydro-1H-pyrazino[1,2-a]quinoxalin-5(6H)-one was reduced to give 0.31 g of product.

The enantiomers were separated by HPLC using a Chirapak AD column with 100% methanol at a flow rate of 0.8 mL/min. The first enantiomer eluted at 7.2 min (Example 5) and the second at 8.9 min (Example 6).

HPLC analysis indicated an ee of >99% (8.9 min retention time).

$[\alpha]^{25}_D$+4.35

$^1$H NMR (400 MHz, $d_6$-DMSO) δ 9.44–9.35 (m, 2H); 6.86 (s, 1H); 6.59 (s, 1H); 3.78 (d, 1H, J=11.8 Hz); 3.37–3.24 (m, 4 H); 3.07–2.89 (m, 3H); 2.69 (m, 1H).

IR (KBr) 3380, 3190, 2970, 2810, 2750, 2400, 1600, 1500, 1450, 1380, 1270, 1140, 1110 cm$^{-1}$.

MS (APCI, m/e (%)) 258 (100, [M+H]$^+$), 260 (65, [M+H]$^+$).

Anal. Calc'd for $C_{11}H_{14}Cl_3N_3$: C, 44.85; H, 4.79; N, 14.26. Found: C, 44.48; H, 4.84; N, 13.71.

EXAMPLE 7
9-Chloro-8-Trifluoromethyl-2,3,4,4a-Tetrahydro-1H-Pyrazino[1,2-a]Quinoxalin-5(6H)-One, Hydrochloride A. 4-Carbobenzyloxy-1-(5-Chloro-2-Nitrophenyl-4-Trifluoromethyl)Piperazine-2-Carboxylic Acid A mixture of 0.98 g of 4-carbobenzyloxypiperazine-2-carboxylic acid, 1.0 g of 2,4-dichloro-5-nitrobenzotrifluoride, and 0.99 mL of diisopropylethylamine in 35 mL of dimethylsulfoxide is heated to 60° C. for 72 hours. After cooling to ambient temperature, the resulting mixture is treated with HCl to pH 3. The mixture is then diluted with $H_2O$ and extracted with ethyl acetate. The combined extracts are dried over $MgSO_4$ and concentrated to give the crude product.

B. 3-Carbobenzyloxy-9-Chloro-8-Trifluoromethyl-2,3,4,4a-Tetrahydro-1H-Pyrazino [1,2-a]Quinoxalin-5(6H)-One Iron powder, 0.64 g, was added in portions to a rapidly stirred solution of 1.8 g of 4-carbobenzyloxy-1-(5-chloro-2-nitrophenyl-4-trifluoromethyl)-piperazine-2-carboxylic acid in 35 mL glacial acetic acid at 50° C. The resulting mixture was stirred overnight at 50° C. After cooling to ambient temperature, the reaction mixture was poured into 20 mL of $H_2O$ and filtered. The solid was washed with 1 N HCl and diethyl ether to give 0.59 g of the desired product as a brown solid.

C. 9-Chloro-8-Trifluoromethyl-2,3,4,4a-Tetrahydro-1H-Pyrazino[1,2-a]Quinoxalin-5(6H)-One, Hydrochloride A mixture of 0.58 g of 3-carbobenzyloxy-9-chloro-8-trifluoromethyl-2,3,4,4a-tetrahydro-1H-pyrazino-[1,2-a]quinoxalin-5(6H)-one and 2.3 g of potassium hydroxide in 12 mL of 50% aqueous methanol was heated to reflux for 2 h. The reaction mixture was concentrated under reduced pressure to approximately half its original volume. The crude material was diluted with 100 mL of ethyl acetate and 100 mL of saturated aqueous sodium bicarbonate. The phases were separated and the aqueous phase was extracted with ethyl acetate. The combined organic phases were dried over $MgSO_4$, filtered, and concentrated. The crude material was dissolved in ethanol and a solution of HCl in ethanol was added until acidic.

The resulting mixture was filtered and the solid was washed with ether. The solid was then dried in a vacuum oven to give 0.21 g (48%) of the desired product as its hydrochloride salt.

$^1$H NMR (400 MHz, $d_6$-DMSO) δ 11.0 (s, 1H); 9.47 (br s, 2H); 7.22 (s, 1H); 7.18 (s, 1H); 4.19 (dd, 1H, J=11.6, 3.2 Hz); 4.01 (d, 1H, J=11.8 Hz); 3.62 (d, 1 H, J=11.7 Hz); 3.41 (d, 1H, J=10.1 Hz); 3.14–3.01 (m, 3H).

IR (KBr) 3460, 3170, 3020, 2970, 2800, 1700, 1620, 1505, 1450, 1400, 1370, 1300, 1230, 1160, 1110 cm$^{-1}$.

MS (APCI, m/e 306 (100, [M+H]$^+$), 308 (33, [M+H]$^+$).

Anal. Calc'd for $C_{12}H_{12}ClF_3N_3O$: C, 42.13; H, 3.54; N, 12.28. Found: C, 41.88; H, 3.71; N, 11.81.

The enantiomers were separated by HPLC using a Chirapak AD column with 85:15 methanol:water (+0.1% diethylamine) at a flow rate of 0.5 mL/min. The first enantiomer (Example 9) eluted at 17.5 min ($[\alpha]^{25}_D$+43) and the second (Example 8) at 22.0 min ($[\alpha]^{25}_D$−40).

EXAMPLE 8
(S)-9-Chloro-8-Trifluoromethyl-2,3,4,4a-Tetrahydro-1H-Pyrazino[1,2-a]-Quinoxalin-5(6H)-One, Hydrochloride The enantiomers were separated by HPLC using a Chirapak AD column with 85:15 methanol:water (+0.1% diethylamine) at a flow rate of 0.5 mL/min. The first enantiomer (Example 9) eluted at 17.5 min ($[\alpha]^{25}_D$+43) and the second (Example 8) at 22.0 min ($[\alpha]^{25}_D$−40).

$^1$H NMR (400 MHz, $d_6$-DMSO) δ 11.0 (s, 1H); 9.47 (br s, 2H); 7.22 (s, 1H); 7.18 (s, 1H); 4.19 (dd, 1H, J=11.6, 3.2 Hz); 4.01 (d, 1H, J=11.8 Hz); 3.62 (d, 1 H, J=11.7 Hz); 3.41 (d, 1H, J=10.1 Hz); 3.14–3.01 (m, 3H).

IR (KBr) 3460, 3170, 3020, 2970, 2800, 1700, 1620, 1505, 1450, 1400, 1370, 1300, 1230, 1160, 1110 cm$^{-1}$.

MS (APCI, m/e 306 (100, [M+H]$^+$), 308 (33, [M+H]$^+$).

$[\alpha]^{25}_D$−40

Anal. Calc'd for $C_{12}H_{12}ClF_3N_3O$: C, 42.13; H, 3.54; N, 12.28. Found: C, 41.59; H, 3.61; N, 12.07.

EXAMPLE 9
(R)-9-Chloro-8-Trifluoromethyl-2,3,4,4a-Tetrahydro-1H-Pyrazino[1,2-a]Quinoxalin-5(6H)-One, Hydrochloride The enantiomers were separated by HPLC using a Chirapak AD column with 85:15 methanol:water (+0.1% diethylamine) at a flow rate of 0.5 mL/min. The first enantiomer (Example 9) eluted at 17.5 min ($[\alpha]^{25}_D$+43) and the second (Example 8) at 22.0 min ($[\alpha]^{25}_D$−40).

HPLC analysis indicated an ee of 96% (17.5 min retention time).

$[\alpha]^{25}_D$+43

$^1$H NMR (400 MHz, $d_6$-DMSO) δ 11.0 (s, 1H); 9.47 (br s, 2H); 7.22 (s, 1H); 7.18 (s, 1H); 4.19 (dd, 1H, J=11.6, 3.2 Hz); 4.01 (d, 1H, J=11.8 Hz); 3.62 (d, 1 H, J=11.7 Hz); 3.41 (d, 1H, J=10.1 Hz); 3.14–3.01 (m, 3H).

IR (KBr) 3460, 3170, 3020, 2970, 2800, 1700, 1620, 1505, 1450, 1400, 1370, 1300, 1230, 1160, 1110 cm$^{-1}$.

MS (APCI, m/e 306 (100, [M+H]$^+$), 308 (33, [M+H]$^+$).

Anal. Calc'd for $C_{12}H_{12}ClF_3N_3O$: C, 42.13; H, 3.54; N, 12.28. Found: C, 41.83; H, 3.49; N, 12.01.

EXAMPLE 10
9,10-Dichloro-2,3,4,4a-Tetrahydro-1H-Pyrazino[1,2-a]Quinoxalin-5(6H)-One. Hydrochloride A. 4-Carbobenzyloxy-1-(5,6-Dichloro-2-Nitrophenyl)Piperazine-2-Carboxylic Acid By the same procedure described for Example 7 A, from 0.86 g of 2,3,4-trichloro-nitro-benzene and 1.0 g of 4-carbobenzyloxypiperazine-2-carboxylic acid, there was obtained 0.75 g of the desired product as a brown oil.

B. 3-Carbobenzyloxy-9,10-Dichloro-2,3,4,4a-Tetrahydro-1H-Pyrazino[1,2-a]Quinoxalin-5(6H)-One By the same procedure described for Example 7 B, from 0.75 g of 4-carbobenzyloxy-1-(5,6-dichloro-2-nitrophenyl)piperazine-2-carboxylic acid and 0.28 g of iron powder, there was obtained 0.34 g (49%) of the desired product as a brown solid.

C. 9,10-Dichloro-2,3,4,4a-Tetrahydro-1H-Pyrazino[1,2-a]Quinoxalin-5(6H)-One, Hydrochloride By the same procedure described for Example 7, from 0.34 g of 4-carbobenzyloxy-1-(5,6-dichloro-2-nitrophenyl)piperazine-2-carboxylic acid and 1.5 g of potassium hydroxide, there was obtained 18 mg of product isolated as its hydrochloride salt.

$^1$H NMR (400 MHz, d$_6$-DMSO) δ 11.1 (s, 1H); 9.05 (br s, 2H); 7.45 (d, 1H, J=8.8 Hz); 6.97 (d, 1H, J=8.8 Hz); 4.06 (d, 1H, J=3.7 Hz); 3.84 (d, 1H, J=13.2 Hz); 3.29–3.12 (m, 4H); 2.77 (m, 1H).

IR (KBr) 3440, 3160, 3020, 2970, 1695, 1570, 1470, 1390, 1280 cm$^{-1}$.

MS (EI, m/e (%) 271 (55, M$^+$), 273 (35, M$^+$).

Anal. Calc'd for $C_{11}H_{12}Cl_3N_3O$: C, 42.81; H, 3.92; N, 13.62. Found: C, 42.40; H, 3.98; N, 12.82.

EXAMPLE 11

7,9-Dichloro-2,3,4,4A-Tetrahydro-1H-Pyrazino[1,2-a]Quinoxalin-5(6H)-One, Hydrochloride The title compound was synthesized according to the method of Example 1, substituting 2,4-dichloro-6-fluoronitrobenzene [Clark, J. H.; Nightengale, D. J. *J. Fluorine Chem.* (1996) 78 (1), 91–93.] for 1,2-dichloro-4-fluoro-5-nitrobenzene. The melting point of the title compound is 308–311° C.

EXAMPLE 12

(R)-9-Chloro-2,3,4,4a-Tetrahydro-1H-Pyrazino[1,2a]Quinoxalin-5(6H)-One

A. (R)-4-Carbobenzyloxy-1-(5-Chloro-2-Nitrophenyl)-Piperazine-2-Carboxylic Acid.

By the same procedure described for example 2 method 2B, from 0.95 g of (R)-4-carbobenzyloxypiperazine-2-carboxylic acid, there was obtained 1.2 g (85.7%) of title compound as a orange solid, mp 145–155° C.

MS (ESI, m/e (%)) 420 (100, [M+H]$^+$) and 422 (40, [M+H]$^+$).

[α]$_D$=+196.0° (c=1, MeOH).

B. (R)-Carbobenzyloxy-9-Chloro-2,3,4,4a-Tetrahydro-1H-Pyrazino[1,2a]Quinoxalin-5(6H)-One.

By the same procedure described for example 2 method 2C, from 1.12 g (R)-4-carbobenzyloxy-1-(5-chloro-2-nitrophenyl)-piperazine-2-carboxylic acid, there was obtained 0.80 g (80.8%) of title compound as a white solid, mp 139–141° C.

H$^1$ (NMR (400 Hz, d$_6$-DMSO) δ 10.73 (s, 1H); 7.38–7.30 (m, 5H); 6.87–6.78 (m, 3H); 5.11 (s, 2H); 4.38 (d, 1H, J=13.0 Hz); 4.06 (d, 1H, J=13.0 Hz); 3.70 (d, 1H, J=11.4 Hz); 3.57 (dd, 1H, J=11.0, 3.7 Hz); 2.97 (bs, 2H); 2.65 (dt, 1H, J=11.3, 3.5 Hz).

MS (APCI, m/e (%)) 372 (100, [M+H]$^+$) and 374 (40, [M+H]$^+$).

Anal. Calc'd for $C_{19}H_{18}ClN_3O_3$: C, 61.38; H, 4.88; N, 11.30. Found: C, 61.46; H, 4.76; N, 11.27.

C. (R)-9-Chloro-2,3,4,4a-Tetrahydro-1H-Pyrazino[1,2a]Quinoxalin-5(6H)-One.

By the same procedure described for example 2 method 2D, from 0.50 g (R)-carbobenzyloxy-9-chloro-2,3,4,4a-tetrahydro-1H-pyrazino[1,2a]-quinoxalin-5(6H)-one, there was obtained 0.27 g (87.1%) of title compound as a white solid, mp 146–149° C.

MS ((+)ESI, m/e (%)) 238 (85, [M+H]$^+$).

Anal. Calc'd for $C_{11}H_{12}ClN_3O$: C, 55.59; H, 5.09; N, 17.68. Found: C, 55.59; H, 4.98; N, 17.40.

[α]$^{25}_D$=+28.9° (c=1, MeOH).

Chiral Purity=99.9% (Chiralpak AD, 4.6×250 mm).

The hydrochloride salt was prepared from HCl and MeOH as a light green solid, mp decomposed 270–280° C.

H$^1$ NMR (400 Hz, d$_6$-DMSO) δ 10.90 (s, 1H); 9.53 (s, 2H); 6.94 (bs, 1H); 6.90–6.84 (m, 2H); 3.96 (dd, 1H, J=13.1, 3.4 Hz); 3.86 (d, 1H, J=11.0 Hz); 3.62 (bd, 1H, J=12.0 Hz); 3.42 (d, 1H, J=10.6 Hz); 3.10–2.97 (m, 3H).

MS (APCI, m/e (%)) 238 (100, [M+H]$^+$) and 240 (40, [M+H]$^+$).

Anal. Calc'd for $C_{11}H_{12}ClN_3O\cdot HCl$: C, 48.19; H, 4.78; N, 15.33. Found: C, 48.38; H, 5.06; N, 14.91.

Chiral Purity=99.9% (Chiralpak AD, 4.6×250 mm).

[α]$_D$=+7.0° (c=1, MeOH).

EXAMPLE 13

8,9-Difluoro-2,3,4,4a-Tetrahydro-1H-Pyrazino[1,2-a]Quinoxalin-5(6H)-One

A. 4-Carbobenzyloxy-1-(4,5-Difluoro-2-Nitrophenyl)-Piperazine-2-Carboxylic Acid.

By the same procedure described for example 2 method 2B, from 1.5 g of racemic 4-carbobenzyloxypiperazine-2-carboxylic acid and 1,2,4-trifluoro-5-nitrobenzene, there was obtained 0.4 g (16.7%) of title compound as an orange-red residue.

MS (APCI, m/e (%)) 422 (45, [M+H]$^+$).

B. 3-Carbobenzyloxy-8,9-Difluoro-2,3,4,4a-Tetrahydro-1H-Pyrazino[1,2-a]Quinoxalin-5(6H)-One.

By the same procedure described for example 2 method 2C, from 0.29 g of 4-carbobenzyloxy-1-(4,5-difluoro-2-nitrophenyl)-piperazine-2-carboxylic acid, there was obtained 0.17 g (66.0%) of title compound as a white solid, mp 226–8° C.

H$^1$ NMR (400 MHz, d$_6$-DMSO) δ 10.70 (s, 1H); 7.39–7.30 (m, 5H); 6.98–6.92 (m, 1H); 6.82–6.77 (m, 1H); 5.11 (s, 2H); 4.38 (d, 1H, J=13.0 Hz); 4.06 (d, 1H, J=13.0 Hz); 3.62 (d, 1H, J=11.0 Hz); 3.52 (dd, 1H, J=11.0, 4.0 Hz); 2.98 (bs, 2H); 2.65 (dt, 1H, J=11.0, 4.0 Hz).

MS (APCI, m/e (%)) 374 (100, [M+H]$^+$).

Anal. Calc'd for $C_{19}H_{17}F_2N_3O_3$: C, 61.12; H, 4.59; N, 11.25. Found: C, 60.79; H, 4.54; N, 10.95.

C. 8,9-Difluoro-2,3,4,4a-Tetrahydro-1H-Pyrazino[1,2-a]Quinoxalin-5(6H)-One

By the same procedure described for example 2 method 2D, from 0.28 g 3-carbobenzyloxy-8,9-difluoro-2,3,4,4a-tetrahydro-1H-pyrazino[1,2-a]quinoxalin-5(6H)-one there was obtained 0.14 g (78.1%) of title compound as a white solid. The hydrochloride salt of this material, prepared from an excess of hydrogen chloride in ethanol, was obtained as a white solid, mp >280° C.

H$^1$ NMR (400 MHz, d$_6$-DMSO) δ 10.89 (s, 1H); 9.57 (s, 2H); 7.07–7.02 (m, 1H); 6.90–6.86 (m, 1H); 3.93 (dd, 1H, J=11.0, 3.0 Hz); 3.77 (d, 1H, J=11.0 Hz); 3.62 (m, 1H); 3.62 (m, 1H); 3.42 (d, 1H, J=10.0 Hz); 3.10–2.95 (m, 3H).

MS ((+)APCI, m/e (%)) 240 (75, [M+H]$^+$).

Anal. Calc'd for $C_{11}H_{11}F_2N_3O$: C, 47.92; H, 4.39; N, 15.24. Found: C, 47.96; H, 4.37; N, 14.86.

What is claimed:

1. A method of treating depression in a mammal comprising administering to a mammal in need thereof an effective amount of a compound of Formula I having the structure

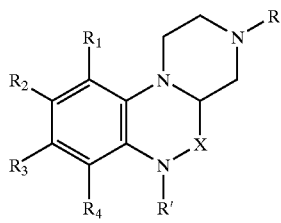

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

2. The method of claim 1, wherein the non-hydrogen substituents of $R_1$, $R_2$, $R_3$, or $R_4$ are halogen or trifluoromethyl.

3. The method of claim 1 wherein the compound is selected from the formulae:

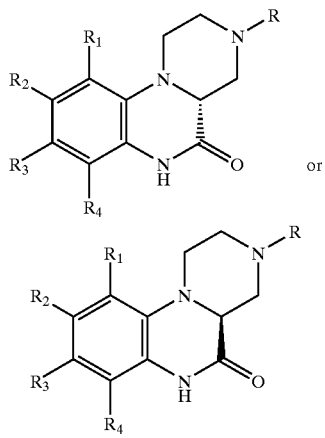

R is hydrogen or alkyl of 1–6 carbon atoms;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

or a pharmaceutically acceptable salt thereof, with the proviso that at least one of $R_1$, $R_2$, $R_3$, or $R_4$ are not hydrogen.

4. The method of claim 3, wherein the non-hydrogen substituents of $R_1$, $R_2$, $R_3$, or $R_4$ are halogen or trifluoromethyl.

5. The method of claim 1 wherein the compound is selected from:

a) 8,9-dichloro-2,3,4,4a-tetrahydro-1H-pyrazino[1,2-a]quinoxalin-5(6H)-one or a pharmaceutically acceptable salt thereof;

b) 8,9-dichloro-2,3,4,4a-tetrahydro-1H-pyrazino[1,2-a]quinoxalin-5(6H)-one hydrochloride salt;

c) (R)-8,9-dichloro-2,3,4,4a-tetrahydro-1H-pyrazino[1,2-a]quinoxalin-5(6H)-one or a pharmaceutically acceptable salt thereof;

d) (R)-8,9-dichloro-2,3,4,4a-tetrahydro-1H-pyrazino[1,2-a]quinoxalin-5(6H)-one hydrochloride salt;

e) (S)-8,9-dichloro-2,3,4,4a-tetrahydro-1H-pyrazino[1,2-a]quinoxalin-5(6H)-one or a pharmaceutically acceptable salt thereof;

f) (S)-8,9-dichloro-2,3,4,4a-tetrahydro-1H-pyrazino[1,2-a]quinoxalin-5(6H)-one hydrochloride salt;

g) 8,9-dichloro-2,3,4,4a,5,6-hexahydro-1H-pyrazino[1,2-a]quinoxaline or a pharmaceutically acceptable salt thereof;

h) 8,9-dichloro-2,3,4,4a,5,6-hexahydro-1H-pyrazino[1,2-a]quinoxaline dihydrochloride salt;

i) (R)-8,9-dichloro-2,3,4,4a,5,6-hexahydro-1H-pyrazino[1,2-a]quinoxaline or a pharmaceutically acceptable salt thereof;

j) (R)-8,9-dichloro-2,3,4,4a,5,6-hexahydro-1H-pyrazino[1,2-a]quinoxaline dihydrochloride salt;

k) (S)-8,9-dichloro-2,3,4,4a,5,6-hexahydro-1H-pyrazino[1,2-a]quinoxaline or a pharmaceutically acceptable salt thereof;

l) (S)-8,9-dichloro-2,3,4,4a,5,6-hexahydro-1H-pyrazino[1,2-a]quinoxaline dihydrochloride salt;

m) 9-chloro-8-trifluoromethyl-2,3,4,4a-tetrahydro-1H-pyrazino[1,2-a]quinoxalin-5(6H)-one or a pharmaceutically acceptable salt thereof;

n) 9-chloro-8-trifluoromethyl-2,3,4,4a-tetrahydro-1H-pyrazino[1,2-a]quinoxalin-5(6H)-one hydrochloride salt;

o) (S)-9-chloro-8-trifluoromethyl-2,3,4,4a-tetrahydro-1H-pyrazino[1,2-a]quinoxalin-5(6H)-one or a pharmaceutically acceptable salt thereof;

p) (S)-9-chloro-8-trifluoromethyl-2,3,4,4a-tetrahydro-1H-pyrazino[1,2-a]quinoxalin-5(6H)-one hydrochloride salt;

q) (R)-9-chloro-8-trifluoromethyl-2,3,4,4a-tetrahydro-1H-pyrazino[1,2-a]quinoxalin-5(6H)-one or a pharmaceutically acceptable salt thereof;

r) (R)-9-chloro-8-trifluoromethyl-2,3,4,4a-tetrahydro-1H-pyrazino[1,2-a]quinoxalin-5(6H)-one hydrochloride salt;

s) 9,10-dichloro-2,3,4,4a-tetrahydro-1H-pyrazino[1,2-a]quinoxalin-5(6H)-one or a pharmaceutically acceptable salt thereof;

t) 9,10-dichloro-2,3,4,4a-tetrahydro-1H-pyrazino[1,2-a]quinoxalin-5(6H)-one hydrochloride salt;

u) 7,9-dichloro-2,3,4,4a-tetrahydro-1H-pyrazino[1,2-a]quinoxalin-5(6H)-one or a pharmaceutically acceptable salt thereof;

v) 7,9-dichloro-2,3,4,4a-tetrahydro-1H-pyrazino[1,2-a]quinoxalin-5(6H)-one hydrochloride salt;

w) (R)-9-chloro-2,3,4,4a-tetrahydro-1H-pyrazino[1,2a]quinoxalin-5(6H)-one or a pharmaceutically acceptable salt thereof;

x) (R)-9-chloro-2,3,4,4a-tetrahydro-1H-pyrazino[1,2a]quinoxalin-5(6H)-one hydrochloride salt;

y) 8,9-difluoro-2,3,4,4a-tetrahydro-1H-pyrazino[1,2-a]quinoxalin-5(6H)-one or a pharmaceutically acceptable salt thereof; or z) 8,9-difluoro-2,3,4,4a-tetrahydro-1H-pyrazino[1,2-a]quinoxalin-5(6H)-one hydrochloride salt.

6. The method of claim 1 wherein the mammal is a human.

7. A method of treating anxiety, obsessive-compulsive disorder, or panic disorder in a mammal comprising administering to a mammal in need thereof an effective amount of a compound of Formula I having the structure

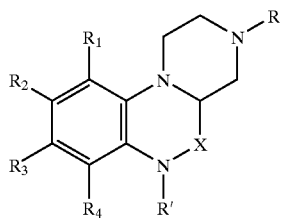

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

8. The method of claim 7, wherein the non-hydrogen substituents of $R_1$, $R_2$, $R_3$, or $R_4$ are halogen or trifluoromethyl and X is a carbonyl moiety.

9. A method of treating migraines in a mammal comprising administering to a mammal in need thereof an effective amount of a compound of Formula I having the structure

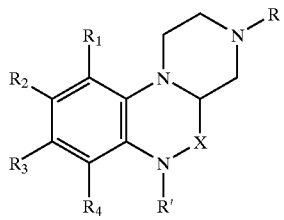

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

10. The method of claim 9, wherein the non-hydrogen substituents of $R_1$, $R_2$, $R_3$, or $R_4$ are halogen or trifluoromethyl and X is a carbonyl moiety.

11. A method of treating eating disorders in a mammal comprising administering to a mammal in need thereof an effective amount of a compound of Formula I having the structure

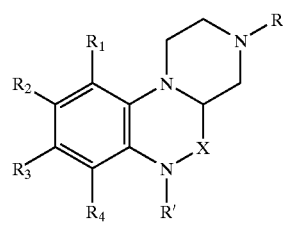

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

12. The method of claim 11, wherein the non-hydrogen substituents of $R_1$, $R_2$, $R_3$, or $R_4$ are halogen or trifluoromethyl and X is a carbonyl moiety.

13. A method of treating type II diabetes in a mammal comprising administering to a mammal in need thereof an effective amount of a compound of Formula I having the structure

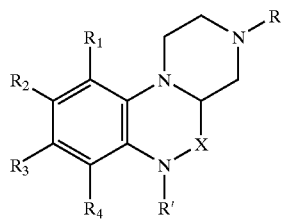

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

14. The method of claim 13, wherein the non-hydrogen substituents of $R_1$, $R_2$, $R_3$, or $R_4$ are halogen or trifluoromethyl and X is a carbonyl moiety.

15. A method of treating epilepsy in a mammal comprising administering to a mammal in need thereof an effective amount of a compound of Formula I having the structure

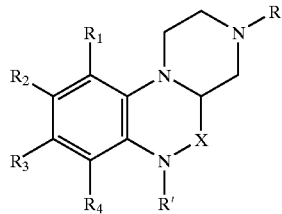

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

16. The method of claim 15, wherein the non-hydrogen substituents of $R_1$, $R_2$, $R_3$, or $R_4$ are halogen or trifluoromethyl and X is a carbonyl moiety.

17. A method of treating sleep disorders in a mammal comprising administering to a mammal in need thereof an effective amount of a compound of Formula I having the structure

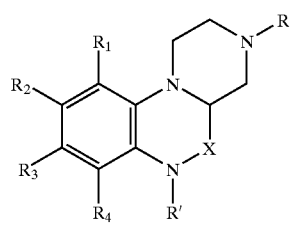

wherein:

R is hydrogen or alkyl of 1–6 carbon atoms;

R' is hydrogen, alkyl of 1–6 carbon atoms, acyl of 2–7 carbon atoms, or aroyl;

$R_1$, $R_2$, $R_3$, and $R_4$ are each, independently, hydrogen, alkyl of 1–6 carbon atoms, alkoxy of 1–6 carbon atoms, halogen, trifluoroalkyl, —CN, alkyl sulfonamide of 1–6 carbon atoms, alkyl amide of 1–6 carbon atoms, amino, alkylamino of 1–6 carbon atoms, dialkylamino of 1–6 carbon atoms per alkyl moiety, trifluoroalkoxy of 1–6 carbon atoms, acyl of 2–7 carbon atoms, or aroyl;

X is $CR_5R_6$ or a carbonyl group;

$R_5$ and $R_6$ are each, independently, hydrogen or alkyl of 1–6 carbon atoms;

or a pharmaceutically acceptable salt thereof, with the proviso that at least one of $R_1$, $R_2$, $R_3$, or $R_4$ are not hydrogen.

18. The method of claim 17, wherein the non-hydrogen substituents of $R_1$, $R_2$, $R_3$, or $R_4$ are halogen or trifluoromethyl and X is a carbonyl moiety.

* * * * *

UNITED STATES PATENT AND TRADEMARK OFFICE
CERTIFICATE OF CORRECTION

| | |
|---|---|
| PATENT NO. | : 6,706,714 B2 |
| DATED | : March 16, 2004 |
| INVENTOR(S) | : Annmarie Louise Sabb, Gregory Scott Welmaker and James Albert Nelson |

It is certified that error appears in the above-identified patent and that said Letters Patent is hereby corrected as shown below:

<u>Title page,</u>
Insert Item -- [73] Assignee: Wyeth, Madison, NJ (US) --.

Signed and Sealed this

Eighteenth Day of October, 2005

JON W. DUDAS
*Director of the United States Patent and Trademark Office*